(12) United States Patent
Platano et al.

(10) Patent No.: US 7,485,464 B2
(45) Date of Patent: Feb. 3, 2009

(54) METHOD AND APPARATUS FOR SAMPLE PREPARATION IN AN AUTOMATED DISCRETE FLUID SAMPLE ANALYZER

(75) Inventors: Joseph Platano, Brookfield, CT (US); Antonio Gagliarducci, Rome (IT); Ausilio Pieralisi, Rome (IT)

(73) Assignee: Westco Scientific Instruments, Inc., Danbury, CT (US)

( * ) Notice: Subject to any disclaimer, the term of this patent is extended or adjusted under 35 U.S.C. 154(b) by 404 days.

(21) Appl. No.: 10/426,893

(22) Filed: Apr. 30, 2003

(65) Prior Publication Data
US 2004/0219062 A1 Nov. 4, 2004

(51) Int. Cl.
*G01N 35/02* (2006.01)
*G01N 1/00* (2006.01)

(52) U.S. Cl. .............. 436/47; 422/63; 422/64; 422/65; 422/67; 422/100; 436/43; 436/49; 436/110; 436/174; 436/180

(58) Field of Classification Search .......... 422/63–67, 422/100; 436/43, 49, 173–181, 47, 110
See application file for complete search history.

(56) References Cited
U.S. PATENT DOCUMENTS

| | | | | |
|---|---|---|---|---|
| 4,451,433 A | * | 5/1984 | Yamashita et al. | 422/63 |
| 4,483,823 A | * | 11/1984 | Umetsu et al. | 422/63 |
| 5,051,238 A | * | 9/1991 | Umetsu et al. | 422/64 |
| 5,320,966 A | * | 6/1994 | Mitsumaki et al. | 436/47 |
| 7,157,059 B1 | * | 1/2007 | Patton et al. | 422/139 |
| 2001/0048899 A1 | * | 12/2001 | Marouiss et al. | 422/100 |

OTHER PUBLICATIONS van Staden, J. F. et al, Fresenius' Zeitschrift fuer Analytische Chemie 1986, 325, 150-152.*
Torres, P. et al, Analytica Chimica Acta 1995, 308, 371-377.*
Sakamoto, C. M. et al, Deep-Sea Research I 1996, 43, 1763-1775.*
Navarro-Gonzalvez, J. A. et al, Clinical Chemistry 1998, 44, 679-681.*

(Continued)

*Primary Examiner*—Arlen Soderquist
(74) *Attorney, Agent, or Firm*—King & Spalding LLP (57) ABSTRACT

An automated discrete fluid sample analyzer includes a sample preparation module. The sample preparation module includes a well configured to receive a sample deposited by a pipettor and a sample preparation device in fluid communication with the well. The fluid sample is transferred from the well to the sample preparation device, and the sample preparation device prepares the fluid sample. The pipettor then aspirates the prepared fluid sample. The prepared fluid sample may be transferred from the sample preparation device back to the well, and the pipettor aspirates the prepared fluid sample from the well. In one embodiment, the sample preparation device includes a receptacle having a catalyst disposed therein. The catalyst may include a noble metal catalyst, such as cadmium. In another embodiment, the sample preparation device includes an ultraviolet lamp configured to apply ultraviolet light to the fluid sample. In yet another embodiment, the sample preparation device includes a heater configured to heat the fluid sample. In another aspect, a fluid sample is agitated to place more of the fluid sample in contact with the catalyst.

14 Claims, 6 Drawing Sheets

OTHER PUBLICATIONS

Velasco-Arjona, A. et al, Talanta 1998, 46, 969-976.*
Vereda Alonso, E. et al, Analyst 1998, 123, 1561-1564.*
Masserini, R. T. et al, Marine Chemistry 2000, 68, 323-333.*
Sun, B. et al, Laboratory Robotics and Automation 2000, 12, 312-316.*
Petsul, P. H. et al, Analytica Chimica Acta 2001, 428, 155-161.*
Legnerova, Z. et al, Water Research 2002, 36, 2777-2783.*
Harris, S. J. et al, International Journal of Environmental Analytical Chemistry 2002, 82, 369-376.*
Oms, M. T. et al, Talanta 2003, 59, 319-326.*
St.-Jean, R. et al, Environmental Letters 1974, 6, 193-203.*
Ramirez-Munoz, J., Analytica Chimica Acta 1974, 72, 437-442.*
Davison, W. et al, Analyst 1978, 103, 403-406.*
Marsh, J. A. P. et al, Analyst 1979, 104, 136-142.*
Biosca, C. et al, Journal of Automatic Chemistry 1989, 11, 159-163.*
Hitachi 717 Analyzer for Sale http://www.labx.com/v2/adsearch/detail3.cfm?adnumb=349336&rv=1 Posted: Sunday, Feb. 24, 2008.*
Krottinger, D. L. et al, The journal of Automatic Chemistry 1978, 1, 15-21.*
Koupparis, M. A. et al, The Journal of Automatic Chemistry 1980, 2, 66-75.*
Converse, J. G., Process Control and Quality 1993, 5, 131-136.*
Cernocka, H, et al, Scipta13 Chemistry 1996, 25, 37-46.*
Mikuska, P. et al, Chemia i Inzynieria Ekologiczna 2001, 8, 115-120.*
SmartChem analyzer images from the internet dated Oct. 23, 2001 one page two images.*

* cited by examiner

METHOD AND APPARATUS FOR SAMPLE PREPARATION IN AN AUTOMATED DISCRETE FLUID SAMPLE ANALYZER

BACKGROUND OF THE INVENTION

The present invention relates to automated discrete fluid sample analyzers and, more particularly, to sample preparation in automated discrete fluid sample analyzers.

Analysis of a fluid sample typically requires measuring a volume of the sample, applying one or more reagents, buffers, or catalysts to the sample, and assaying the sample using a device such as a calorimeter, photometer, or the like. For example, in the testing of fluids (e.g., water) for nitrate content, a predetermined amount of the fluid is combined with a predetermined amount of a buffer (e.g., ammonium chloride). The fluid sample is then applied to a catalyst, such as cadmium, to reduce the nitrates into nitrites. After reduction, the fluid sample is then assayed using a colorimeter to determine the nitrite content of the sample, which correlates to the nitrate content. Where a large number of samples are to be analyzed, manually performing this process can be time consuming, costly, and inconsistent.

Out of the need to reduce costs and improve consistency, Continuous Flow Analysis (CFA) was developed. With CFA, a series of fluid samples, each of which may be mixed with one or more reagents and/or buffers, are pumped through a tubing path. Each fluid sample within the tubing path is separated from adjacent fluid samples by air bubbles, which act to clean the tubing path between fluid samples. The tubing path may include a tube formed from a catalyst, such as cadmium, through which each fluid sample flows to reduce the fluid sample. The series of fluid samples continues along the tubing path where each fluid sample in the series is individually assayed using a device such as a calorimeter photometer, or the like.

The advent of CFA has improved productivity and consistency. Unfortunately, lengthy start-up and shut-down times make CFA time consuming for small analysis runs. In addition, operator technique in setting up and performing each analysis run plays a significant role in the quality of the data obtained using CFA.

To further reduce costs and improve consistency, automated discrete analysis techniques were developed. Automated discrete analysis techniques use computer-controlled automation to perform steps similar to those of the manual method. For example, a computer-controlled robotic arm may be used to position a probe of a pipettor to aspirate or deposit a fluid sample, buffer, or reagent into or out of any of a plurality of sample receptacles, a plurality of reagent receptacles, and a plurality of reaction cuvettes. This is a "discrete" analysis technique because each sample is deposited in a discrete reaction cuvette, which is then subjected to an assaying device such as a calorimeter photometer, or the like.

Automated discrete analysis techniques provide many advantages over CFA. First, because the analysis is discrete, certain variables associated with CFA (e.g., developing and maintaining correct bubble patterns, obtaining baseline readings, and carryover between samples) are eliminated. As a result, operator technique is not as critical with automated discrete analysis as it is with CFA. Moreover, because these variables are eliminated, consistency between analyses is improved. Second, the start-up and shut-down times for analysis runs is eliminated. Finally, because pipettors may be used in lieu of peristaltic pumps, variability due to pump tube elongation is eliminated.

However, for certain assays, discrete analysis requires that the samples be prepared either prior to placing them in the sample receptacle or that the run be stopped and the samples removed and prepared prior to continuing the run. For example, in the testing of fluids (e.g., water) for nitrate content, the samples must be reduced before they are assayed. With discrete analysis systems, this requires manually removing the sample, performing the reduction, and replacing the sample. This manual step can be time consuming and inconsistent.

One recent technique used to overcome this limitation is to place a cadmium tube in the fluid sample flow path within the pipettor. When the fluid sample, which is typically mixed with a buffer, is aspirated into the pipettor, the fluid sample comes in contact with the cadmium tube and the nitrates in the fluid sample are reduced.

SUMMARY OF THE INVENTION

The above described drawbacks and deficiencies of the prior art are overcome or alleviated by an automated discrete fluid sample analyzer including a sample preparation module. The sample preparation module includes a well configured to receive a sample deposited by a pipettor and a sample preparation device in fluid communication with the well. The fluid sample is transferred from the well to the sample preparation device, and the sample preparation device prepares the fluid sample. The prepared fluid sample is then aspirated by the pipettor. The prepared fluid sample may be transferred from the sample preparation device back to the well, and the pipettor aspirates the prepared fluid sample from the well. In one embodiment, the sample preparation device includes a receptacle having a catalyst disposed therein. The catalyst may include a noble metal catalyst, such as cadmium. In another embodiment, the sample preparation device includes an ultraviolet lamp configured to apply ultraviolet light to the fluid sample. In yet another embodiment, the sample preparation device includes a heater configured to heat the fluid sample.

In another aspect, a method of sample preparation in an automated discrete fluid sample analyzer includes: depositing a fluid sample from a pipettor into a well having a sample preparation device in fluid communication therewith; pumping the fluid sample from the well into the sample preparation device to provide a prepared sample; and aspirating the prepared sample into the pipettor. The method may further include pumping the prepared sample from the sample preparation module to the well, and wherein the pipettor aspirates the prepared fluid sample from the well. In one embodiment, the sample preparation device includes a receptacle having a catalyst disposed therein. In another embodiment, the sample preparation device includes an ultraviolet light, and in yet another embodiment, the sample preparation device includes a heater.

In another aspect, the automated discrete fluid sample analyzer includes a catalyst disposed within the pipettor and a means for agitating the fluid sample within the pipettor. The fluid sample is moved across the catalyst after the fluid sample is aspirated into the pipettor and before the sample is deposited from the pipettor. The means for agitating may include: a pump operated to create a repeated, abrupt motion of the fluid sample; discontinuities formed on an internal surface of a catalyst tube; a coil formed from the catalyst tube, the coil having a horizontally configured longitudinal axis; bubbles of an inert gas injected into the fluid sample; a baffle formed on a receptacle including the catalyst; and a vibrator device in operable communication with the fluid sample. The catalyst may include cadmium, and may be granulated, formed into a wire, or formed into a tube forming a portion of the pipettor.

In another aspect, a mixture of fluids is prepared in an automated discrete fluid sample analyzer. The automated discrete fluid sample analyzer includes a pipettor movable between a plurality of receptacles and a plurality of reaction cuvettes, and the method includes: determining a first volume of a first fluid and a second volume of a second fluid to be included in the mixture; comparing the first volume and the second volume to determine an order in which the first fluid and the second fluid are to be aspirated by the pipettor; and aspirating the first fluid and the second fluid in the determined order, the first fluid and the second fluid being aspirated such that both the first fluid and the second fluid are present in the pipettor at the same time. The larger of the first volume and the second volume is aspirated before a smaller of the first volume and the second volume.

The above-described and other features will be appreciated and understood by those skilled in the art from the following detailed description, drawings, and appended claims.

BRIEF DESCRIPTION OF THE DRAWINGS

Referring now to the figures wherein the like elements are numbered alike.

DESCRIPTION OF THE PREFERRED EMBODIMENT

Figure 1:
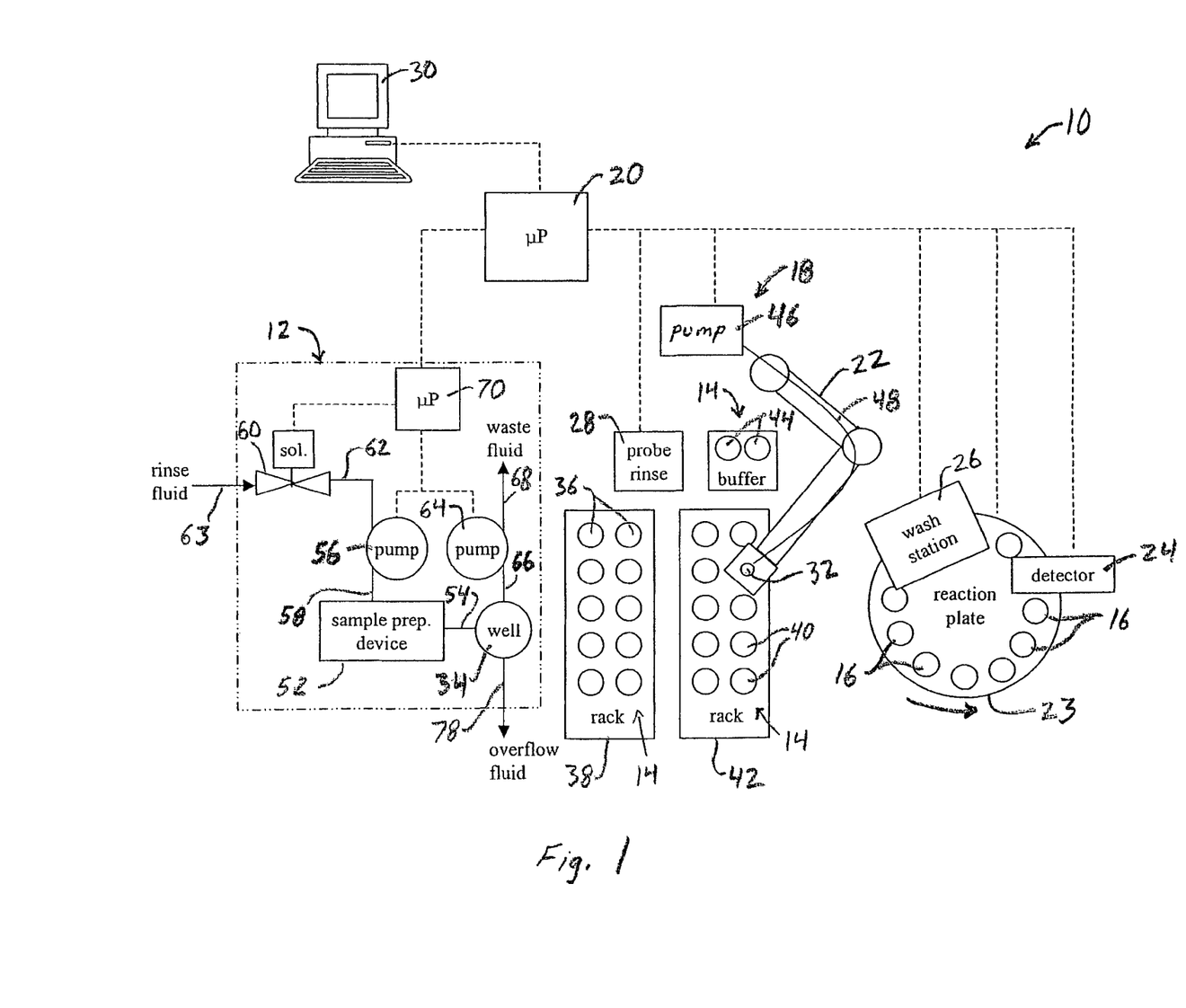
FIG. 1 is a schematic view of an automated discrete fluid sample analyzer including a sample preparation module.

Referring to FIG. 1, a schematic view of an automated discrete fluid sample analyzer 10 including a sample preparation module 12 is shown. The automated discrete fluid sample analyzer 10 is of the type including a pipettor 18 movable between a plurality of receptacles 14 and a plurality of reaction cuvettes 16.

In the embodiment shown, the automated discrete fluid sample analyzer 10 includes a microprocessor 20 operatively coupled to the pipettor 18, an actuator 22, a reaction plate 23, a detector 24, a cuvette wash station 26, a probe rinse station 28, and the sample preparation module 12. Microprocessor 20 receives input from a workstation computer 30, which is programmed with a user-interface module for accepting user input information to define the analyses to be performed by the analyzer 10. Microprocessor 20 applies the user input information to coordinate the operation of the various components of the analyzer 10.

Microprocessor 20 controls the actuator 22 to position a probe 32, which forms a distal end of the pipettor 18, at a selected component of the analyzer 10. For example probe 32 may be positioned at any one of the receptacles 14, reaction cuvettes 16, probe rinse station 28, and a well 34 included in the sample preparation module 12. The receptacles 14 may include a plurality of sample receptacles 36 disposed in one or more sample racks 38, a plurality of reagent receptacles 40 disposed in one or more reagent racks 42, and one or more buffer solution receptacles 44. In the embodiment shown, actuator 22 is a robotic arm. It will be appreciated, however, that actuator 22 may include any computer-controlled device that moves probe 32 of the pipettor 18 relative to the receptacles 14, cuvettes 16, and other components of the analyzer 10 in random access fashion.

The microprocessor 20 also controls the pipettor 18 to aspirate a predetermined amount of sample fluid, reagent, buffer solution, and the like from the selected receptacle 14. Similarly, the microprocessor 20 controls the pipettor 18 to deposit a predetermined amount of the aspirated fluid, reagent, buffer solution, and the like into a receptacle 14 or cuvette 16, or well 34. The pipettor 18 includes the probe 32 and a pump 46, which is in fluid communication with the probe 32. The pump 46 may include any device that develops a vacuum for aspirating a predetermined amount of fluid into the pipettor 18 via the probe 32, and which either breaks this vacuum or develops a positive force to deposit the fluid from the pipettor 18 via the probe 32. For example, the pump 46 may include a vacuum pump, a piston or syringe, or a peristaltic pump. The pump 46 may be coupled to the probe 32 via a length of tubing 48. The pipettor 18 may include a heater for heating the aspirated fluid to a predetermined temperature prior to depositing the fluid. Also, the pipettor 18 may include a level sensor integral to the probe 32 to detect fluid levels in the receptacles 14 and cuvettes 16 and to ensure a proper insertion depth of the probe 32 into the fluid within the receptacles 14 and cuvette 16.

Between aspiration and/or deposit evolution, the probe 32 may be positioned at the probe rinse station 28. The probe rinse station 28 provides a rinse solution to prevent carryover between fluid samples. The probe rinse station 28 may be used to rinse the exterior of the probe 32 by dipping the probe 32 into the rinse station 28, and may also be used to rinse the interior portions of pipettor 18 by dispensing probe rinse into the rinse station 28.

The reaction cuvettes 16 are mounted on the reaction plate 22, which rotates to deliver the cuvettes 16 to the detector 24 and the wash station 26. Detector 24 may include any detector for assaying the fluid sample and providing an output signal indicative of the desired properties to the microprocessor 20. For example, detector 24 may include one or more of a calorimeter, a photometer, a conductance meter, and the like. Wash station 26 washes the reaction cuvettes 16 between each use to allow for continuous operation of the analyzer 10 for any number of fluid samples. The wash station 26 employing one or more rinsing, scrubbing, and checking steps to ensure that the cuvettes 16 are clean.

Figure 2:
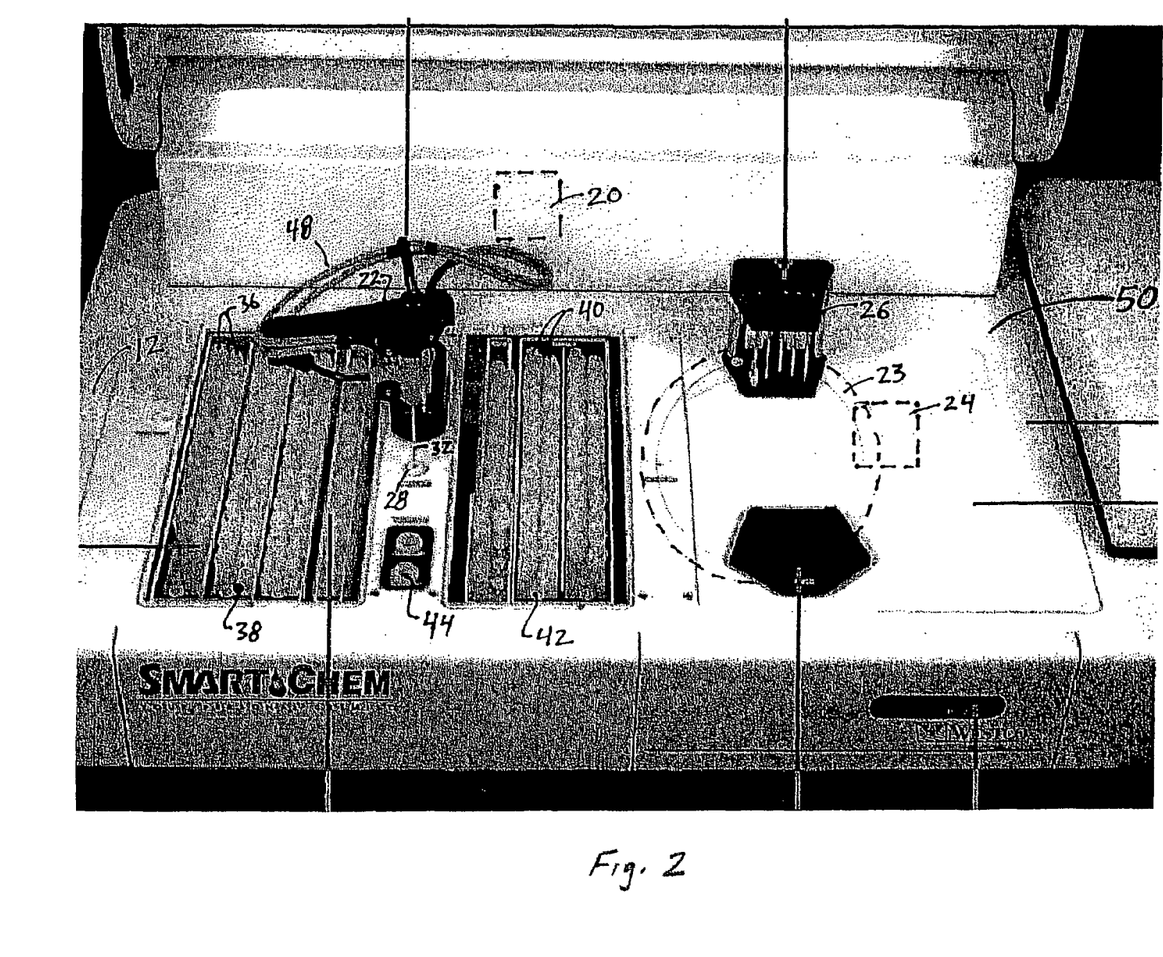
FIG. 2 is a perspective view of the automated discrete fluid sample analyzer including the sample preparation module.

Referring to FIG. 2, the various components of the automated discrete fluid sample analyzer 10, including the sample preparation module 12, are shown mounted in a common housing 50.

Referring again to FIG. 1, the sample preparation module 12 includes well 34, which is configured to receive a fluid sample deposited by the pipettor 18. The fluid sample may be buffered and/or mixed with one or more reagents. The sample preparation module 12 further includes a sample preparation device 52 in fluid communication with the well 34 via tubing 54, and a pump 56 that operates to transfer the fluid sample from the well 34 to the sample preparation device 52 via tubing 54, 58. The sample preparation device 52 prepares the fluid sample, and the pump 56 returns the prepared fluid sample to the well 34 via tubing 52, where the pipettor 18 aspirates the prepared fluid sample using the probe 32. The preparation performed by sample preparation device may include, for example, reducing, distilling, or digesting the fluid sample.

Pump 56 is also in fluid communication with a source of rinse fluid (e.g., ammonium chloride) via a solenoid valve 60 and tubing 62, 63. Solenoid valve 60 selectively interrupts the flow of rinse fluid to the pump 56. When valve 60 is opened, pump 56 is operated to force rinse fluid through the sample preparation device 52 into the well 34 to clean the sample preparation device 52 and the well 34 between fluid samples and, thus, prevent carryover between fluid samples. Pump 56 may be any pump that effectively transfers the fluid sample between the well 34 and the sample preparation device 52. Preferably, pump 56 is a persistaltic pump driven by a reversible stepper motor. However, pump 56 may also include a piston (plunger) pump or the like.

The sample preparation module 12 may also include a second pump 64 in fluid communication with the well 34 via tubing 66, and in fluid communication with a waste fluid destination via tubing 68. Pump 64 transfers rinse fluid from the well 34 to the waste fluid destination to clear the rinse fluid from the well 34 so that the well 34 can receive the next fluid sample.

In the embodiment shown, operation of the pumps 56, 64 and solenoid valve 60 are coordinated by microprocessor 20 through a second microprocessor 70. Microprocessor 20 provides commands to operate the pumps 56, 64 and solenoid valve 60 such that the operation of these devices are coordinated with the pipettor 18. Microprocessor 70 receives these commands and, in response, activates the appropriate pumps 56, 64 and solenoid valve 60. While the present embodiment employs a second microprocessor 70 to activate the pumps 56, 64 and solenoid valve 60, it will be appreciated that microprocessor 20 may directly control the pumps 56, 64 and solenoid valve 60.

Figure 3:
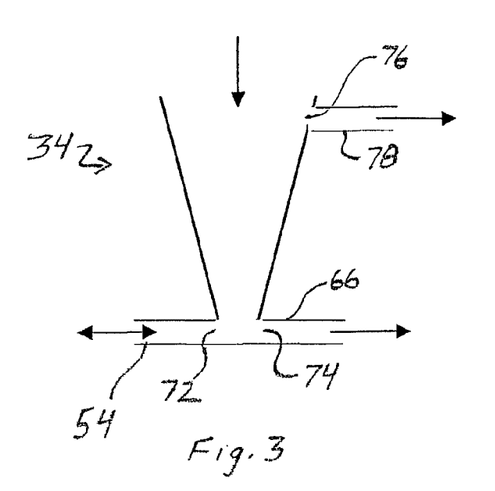
FIG. 3 is a schematic view of a well used in the sample preparation module.

Referring to FIG. 3, the well 34 is shown as a cup-shaped structure having a port 72 disposed at its bottom surface for receiving tubing 54, which provides fluid communication between the well 34 and the sample preparation device 52. The well 34 also includes a port 74 disposed at its bottom surface for receiving tubing 66, which provides fluid communication between the well 34 and the pump 64 for the egress of rinse fluid. The well 34 may also include an overflow channel 76 disposed near its top edge. The overflow channel 76 allows excess fluid to be directed from the well 34 to an overflow fluid receptacle via tubing 78.

Figure 4:
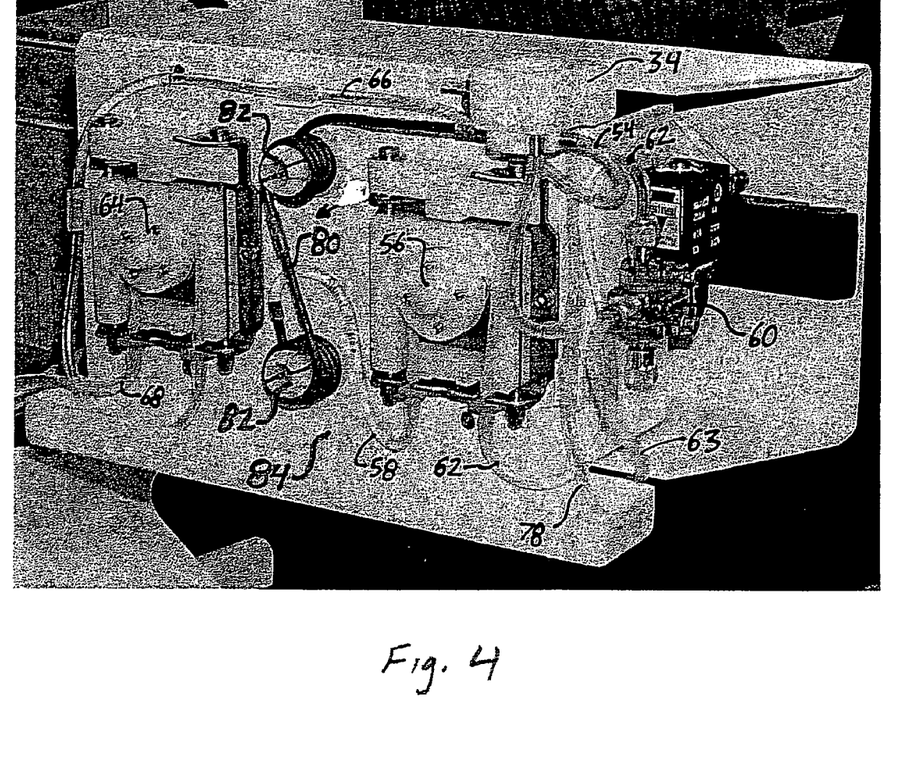
FIG. 4 is a perspective view of the sample preparation module removed from the automated discrete fluid sample analyzer.

Referring to FIG. 4, a perspective view of the sample preparation module removed from the automated discrete fluid sample analyzer 10 is shown. In the embodiment of FIG. 4, the sample preparation device 52 is shown as a tube 80 formed from a catalyst. The catalyst is preferably a noble metal catalyst, and, more preferably, the catalyst is cadmium. Such a sample preparation device 52 would be used, for example, in performing a nitrate reduction on the fluid sample. The tube 80 is coiled around dowels 82 extending from a support structure 84. One end of the tube 80 is coupled to the well 34 via tubing 54, and the other end of the tube 80 is coupled to the pump 56 via tubing 58. Also mounted on the support structure 84 are the well 34, the pumps 56, 64, and the valve 60.

Referring to FIGS. 1 through 4, operation of the automated discrete fluid sample analyzer 10 can be described by way of an example in which a fluid is to be tested for nitrate content. Prior to starting the analysis, a technician fills the sample receptacles 36, reagent receptacles 40, and buffer solution receptacles 44 with the fluid to be tested, appropriate reagents, and a buffer solution, respectively. Operation of the analyzer 10 commences with a priming of the pumps 46 and 56 with rinse solution or the like, as well as any other preliminary steps needed for preparing the analyzer 10 (e.g., washing of the cuvettes 16, performing baseline readings on water samples, etc.) After the analyzer 10 has been prepared, the actuator 22 positions the probe 32 proximate one of the sample receptacles 36, and the pipettor 18 aspirating a predetermined amount of the fluid from the sample receptacle 36. The actuator 22 then positions the probe 32 proximate one of the buffer receptacles 44 and aspirates the buffer solution to buffer the fluid sample to be tested. The actuator 22 then positions the probe 32 proximate the well 34 and deposits the buffered fluid sample into the well 34. Alternatively, the fluid sample to be tested is mixed with the buffer solution in the well 34 rather than in the pipettor 18. In either case, the buffered fluid sample is drawn from the well 34 into the sample preparation device 52 by operation of the pump 56. Within the sample preparation device 52, the buffered fluid sample comes in contact with the catalyst, which acts to reduce the nitrates in the buffered fluid sample to nitrites. As will be described in further detail below, the buffered fluid sample may be moved in a repeated start-stop or repeated back and forth motion across the catalyst. After a predetermined amount of time, the reduced fluid sample is transferred from the sample preparation device 52 to the well 34 by operation of the pump 56, and the pipettor 18 aspirates the reduced fluid sample from the well 34 via the probe 32. The actuator 22 then positions the probe 32 proximate one of the reaction cuvettes 16 and deposits the reduced fluid sample into the reaction cuvette 16. The actuator 22 then moves the probe 32 to aspirate one or more appropriate reagents from a reagent receptacle 40, and then moves the probe 32 to deposit the reagents into the reaction cuvette 16 containing the reduced fluid sample. Rotation of the reaction plate 23 brings the cuvette 16 containing the mixture of the reduced fluid sample and reagents into association with the detector 24 (e.g., a calorimeter), which assays the nitrite content of the mixture. Further rotation of the reaction plate 23 brings the reaction cuvette 16 containing the mixture into association with the wash station 26, which is operated to clean the mixture from the reaction cuvette 16 so that the reaction cuvette 16 may be used for a subsequent sample.

In the sample preparation module 12, after the reduced fluid sample is aspirated by the pipettor 18 from the well 34, solenoid valve 60 is opened and pump 56 is operated to direct the rinse fluid through the sample preparation device 52 into the well 34. Pump 64 is also operated to draw the rinse fluid from the well 34 and provide it to the waste fluid destination. After a sufficient amount of rinse fluid has passed through sample preparation device 52 and well 34 to remove any residue, valve 60 is closed and operation of pump 56 is stopped to interrupt the flow of the rinse fluid. After the well 34 is clear of rinse fluid, pump 64 is stopped. The sample preparation module 12 is now ready to receive the next fluid sample from the pipettor 18.

The sample preparation module 12 allows sample preparation to be performed in one continuous, commonly controlled operation (on-line) rather that separate operations requiring separate pieces of equipment. Accordingly, the sample preparation module 12 eliminates the manual steps that were previously required with automated discrete fluid sample analyzers of the prior art, which required that the samples be prepared either prior to placing them in the sample receptacle or that the run be stopped and the samples removed and prepared prior to continuing the run. As a result, the sample preparation module 12 reduces time and labor costs needed for sample preparation and provides an increased consistency between analysis runs. In addition, as is described hereinafter, the sample preparation module 12 allows different methods of sample preparation, including reduction, distillation, and digestion, to be performed.

As described in the above example, the pipettor 18 may aspirate more than one volume of fluid before depositing the more than one volume of fluid into the well 34 or any receptacle 14 or cuvette 16. This action is typically performed to save time through the efficient operation of the actuator 22 when a mixing of the fluids is desired. It has been determined, however, that the two volumes remain relatively unmixed within the pipettor 18, and that most of the mixing is accomplished by the agitation of the fluid as the fluid is deposited into, and contacts the surfaces of, the well 34, receptacle 14, or cuvette 16. It has been further determined that the order in which the various volumes of fluid are aspirated into the pipettor 18, and hence the order in which these volumes are deposited from the pipettor 18, has an affect on the degree of mixing accomplished when the volumes of fluid are deposited. More specifically, if a larger volume of a first fluid is aspirated before a smaller volume of a second fluid, a higher degree of mixing of the first and second fluids is accomplished than if the smaller volume is aspirated first. While not wanting to be bound by theory, it is believed that the higher degree of mixing is accomplished because, when the larger volume is aspirated before the smaller volume, the smaller volume is subsequently deposited before the larger volume. As a result, the smaller volume is first deposited into the well 34, receptacle 14, or cuvette 16 and is then agitated by the larger volume of fluid as it is deposited into the well 34, receptacle 14, or cuvette 16. The agitation of the smaller volume of fluid causes it to mix with the larger volume of fluid. Accordingly, microprocessor 20 may control actuator 22 and pipettor 18 such that, when pipettor 18 is to aspirate more than one fluid to create a mixture, the fluids in the mixture are aspirated in descending order by volume. That is, pipettor 18 first aspirates the fluid in the mixture having the largest volume, then aspirates the fluid in the mixture having the next largest volume, and so on.

Figure 5:
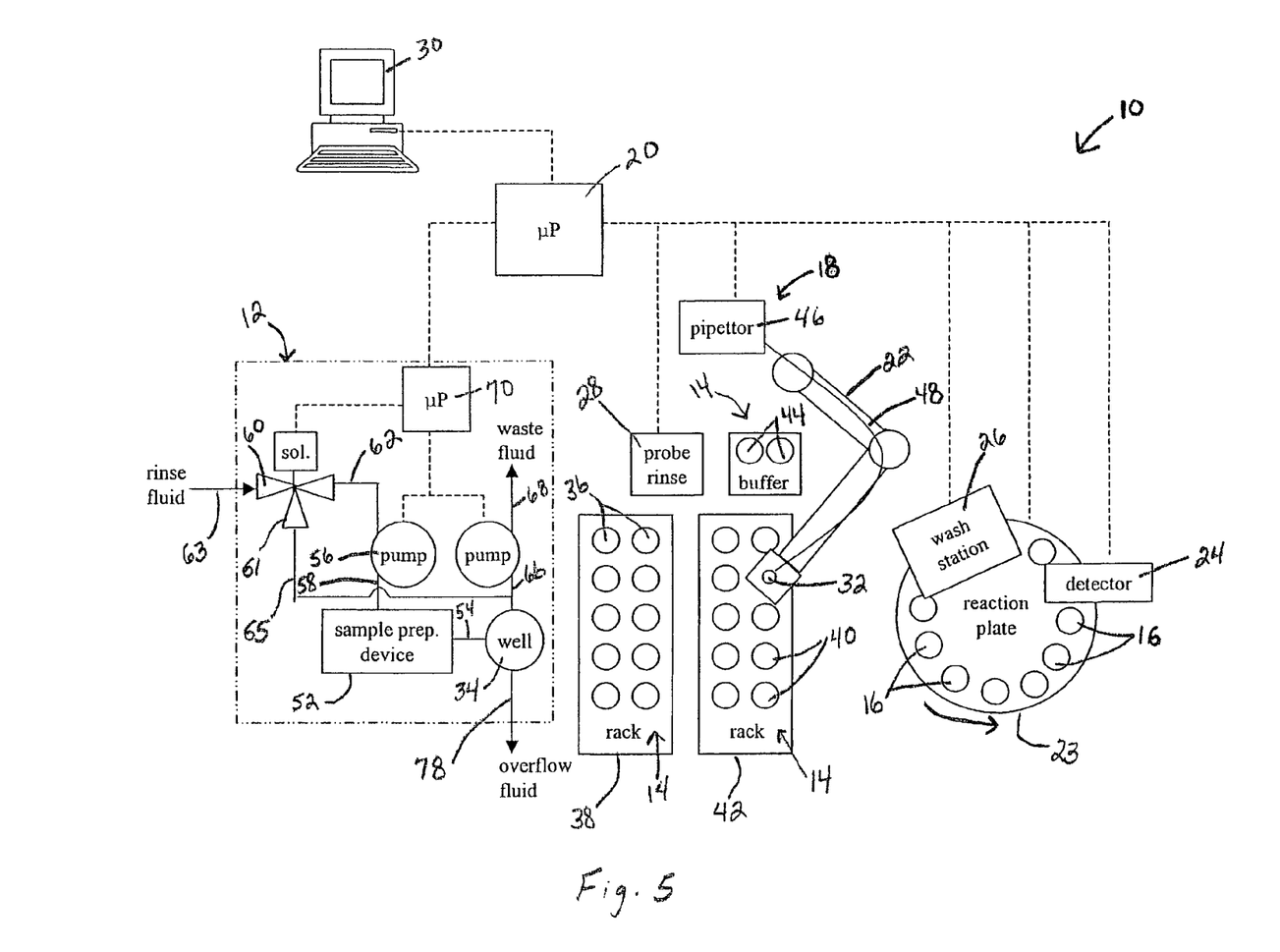
FIG. 5 is a schematic view of an automated discrete fluid sample analyzer including an alternative embodiment of the sample preparation module.

Referring to FIG. 5, a schematic view of automated discrete fluid sample analyzer 10 including an alternative embodiment of the sample preparation module 12 is shown. In this embodiment, solenoid valve 60 is a three-way valve in fluid communication between pump 56, rinse fluid 63, and well 34. For example, one port 61 of the valve 60 may be coupled to well 34 via tubing 65 and 66. In this embodiment, operation of the sample preparation module 12 is as described above, with the additional function of allowing valve 60 to be positioned to provide a circuitous fluid path between pump 56, sample preparation device 52, well 34, and valve 60. With valve 60 positioned to provide this fluid path, the fluid sample may be recirculated any number of times through the sample preparation device 52.

Figure 6:
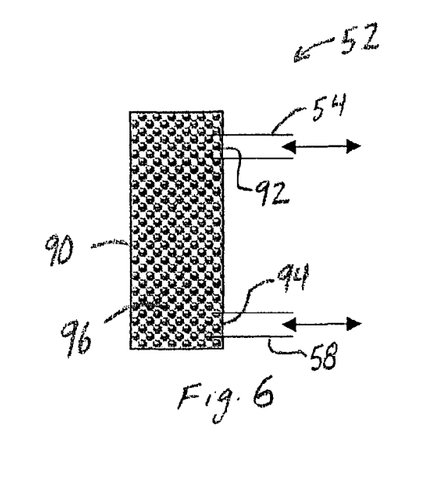
FIG. 6 is an alternative embodiment of a sample preparation device for use in the sample preparation module.
Figure 7:
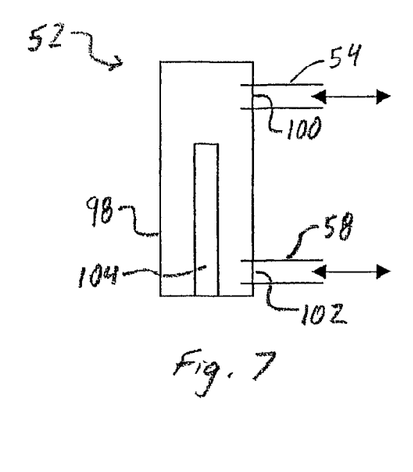
FIG. 7 is another alternative embodiment of a sample preparation device for use in the sample preparation module.
Figure 8:
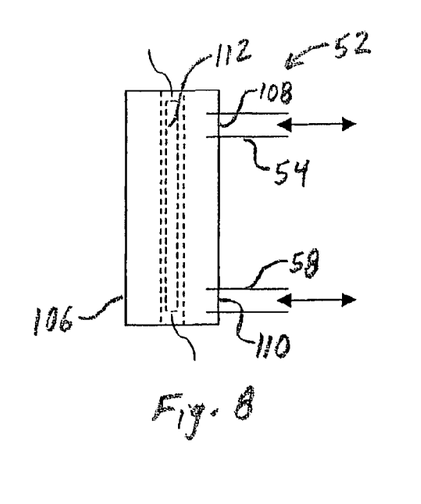
FIG. 8 is another alternative embodiment of a sample preparation device for use in the sample preparation module.

Referring to FIGS. 6 through 8, other embodiments of the sample preparation device 52 are shown. In FIG. 6 the sample preparation device 52 includes a receptacle 90 having ports 92, 94 disposed therein for fluid communication with the well 34 and the pump 56 via tubing 54, 58. The receptacle 90 includes a catalyst 96 including granulated cadmium disposed therein. Alternatively, the receptacle 90 may include wires formed from cadmium disposed therein. In FIG. 7 the sample preparation device 52 includes a receptacle 98 having ports 100, 102 disposed therein for fluid communication with the well 34 and the pump 64 via tubing 54, 58. Disposed within, or located proximate to, the receptacle 98 is a heating element 104. The heating element 104 heats the sample fluid within the receptacle 98 to perform, for example, a distillation of the sample. In FIG. 8 the sample preparation device 52 includes a receptacle 106 having ports 108, 110 disposed therein for fluid communication with the well 34 and the pump 64 via tubing 54, 58. The sample preparation device 52 also includes an ultraviolet (UV) light 112 disposed within a passage formed in the receptacle 106. The receptacle 106 may be formed from a transparent material such as, for example, glass, to allow the UV rays to reach the fluid sample in the receptacle 106. The sample preparation device 52 of FIG. 8 may be used, for example, to digest the fluid sample in the receptacle 52. Each of these different sample preparation devices 52 may be added or removed from sample preparation module 12 as they are needed for a particular analysis run. This provides cost savings in that only the sample preparation device 52 needs to be changed, while most of the other components of the sample preparation module 12 can be reused. While these various examples of sample preparation device 52 are shown, it will be appreciated that sample preparation device 52 may be configured for any method of sample preparation.

Where the sample preparation device 52 includes a catalyst, such as that described with reference to FIGS. 4 and 6, the level of reduction obtained by passing the fluid sample over the catalyst is determined, in general, by the amount of fluid in contact with the catalyst. It has been determined that by agitating the fluid sample as it passes over the catalyst, the level of reduction can be increased over that possible with simply aspirating the fluid sample into the catalyst. While not wanting to be bound by theory, it is believed that the agitation of the fluid brings more of the volume of fluid into contact with the catalyst. Thus, where the sample preparation device 52 includes a catalyst, one or more means for agitating the fluid sample may be employed.

One means for agitating the fluid sample is to operate pump 56 to create repeated, abrupt motion of the fluid. For example, as pump 56 operates to draw the fluid sample from the well 34 to the sample preparation device 52, the pump 56 may be powered in short bursts to draw the fluid in a repeated start and stop manner. Pump 56 may be operated similarly when providing the fluid sample from the sample preparation device 52 to the well 34. Alternatively, pump 56 may be operated to move the fluid in a repeated back and forth manner across the catalyst. As used herein, the term "repeated back and forth motion" includes any motion of the fluid caused by the operation of a pump to move the fluid back and forth across the catalyst in addition to the motion of the fluid needed for simply aspirating and depositing the fluid. For example, in FIG. 1, the pump 56 may operate to aspirate the fluid into the catalyst, force the fluid in a first direction across the catalyst, force the fluid in a second direction opposite the first direction across the catalyst, and then provide a force to deposit the fluid. In this example, the repeated back and forth motion of the fluid is the motion of the fluid in the first and second directions. The distance that the fluid travels during the repeated back and forth motion, the time duration of the repeated back and forth motion, and the number of times the repeated back and forth motion is performed are selected based on the level of reduction desired.

Another means for agitating the fluid sample is to configure the receptacle or tube including the catalyst in a manner that promotes agitation of the fluid. For example, the tube 80 of FIG. 4 may be constructed such that the inside (fluid contacting) surfaces of the tube include irregularities that cause agitation of the flow. Such irregularities may be formed, for example, by peening the tube to create small indentations. In yet another example, where a tube formed from a catalyst is used, such as tube 80 in FIG. 4, the tube may be coiled, with the coil having a longitudinal axis extending through the center of the coil, and the longitudinal axis being oriented horizontally. It has been determined that positioning the longitudinal axis of the coil horizontally promotes agitation. In another example, the receptacle including the catalyst may be formed with flow baffles for agitating the flow.

Another means for agitating the fluid sample is to configure the catalyst in a manner that promotes agitation of the fluid. For example, the catalyst may be granulated and formed in a bed through which the fluid passes, as shown in FIG. 6. In another example, the catalyst may be formed in an irregular shape, which would cause the fluid to agitate as it passed over the catalyst.

Another means for agitating the fluid sample is to couple a vibrator device to the sample preparation device 56. This may include, for example, vibrating the tube or catalyst receptacle using a mechanical vibrator device. This may also include, for example, imparting ultrasonic sound waves onto the fluid sample.

Another means for agitating the fluid sample is to inject bubbles of an inert gas such as, for example, Nitrogen through the wall of the sample preparation device 56 into the fluid sample. Passage of the bubbles through the fluid sample act to agitate the fluid sample.

Figure 9:
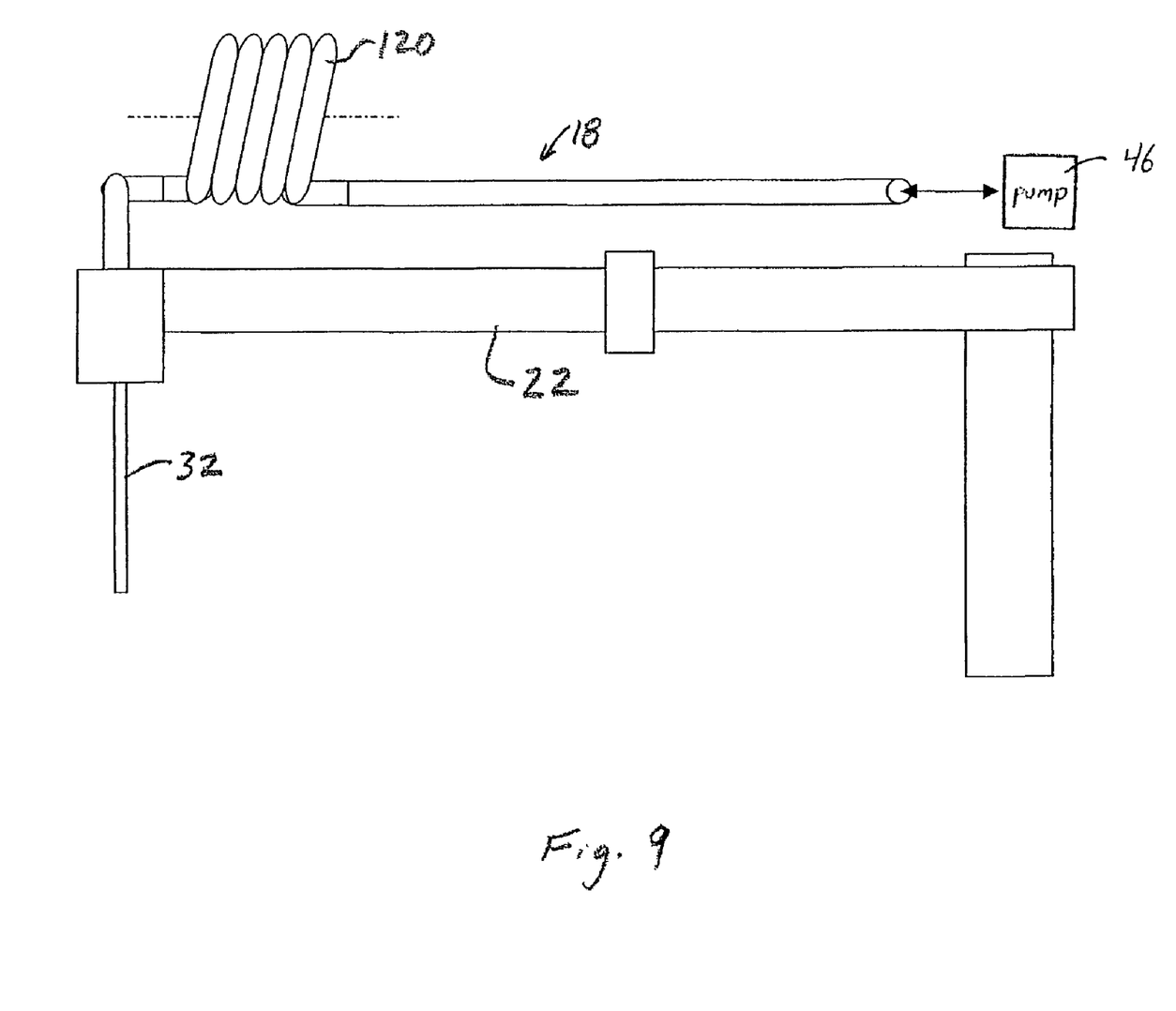
FIG. 9 is an elevation view of a portion of a pipettor mounted to an actuator, the portion of the pipettor including a catalyst.

Referring to FIG. 9, it can be seen that the above means of agitating the fluid sample can be applied to different sample preparation arrangements. In FIG. 9, a cadmium tube 120 is placed in the fluid sample flow path within the pipettor 18 to form a sample preparation device. When the fluid sample is aspirated into the pipettor 18, the fluid sample comes in contact with the cadmium tube 120 and the nitrates in the fluid sample are reduced. The above means for agitating the fluid sample can be applied to this sample preparation arrangement. For example, the pump 46 may be operated to create repeated, abrupt motion of the fluid. In another example, the tube 120 or other catalyst receptacle fitted to pipettor 18 may be configured to promote agitation of the fluid, or the catalyst within the receptacle may be configured in a manner that promotes agitation of the fluid. In yet another example, the tube 120 can be vibrated using a vibrating device.

In designs of the prior art, an increased level of reduction was typically obtained by increasing the length of the tube 120. Problematically, however, the longer the length of the tube 120, the more costly it is. Moreover, because the catalyst used in tube 120 is likely to be considered hazardous material (e.g., cadmium), as the length of the tube 120 increases, the amount of hazardous material associated with the tube 120 also increases. By agitating the fluid sample as it flows across the catalyst, the same level of reduction can be obtained with a shorter length of tube or with less catalyst. This results in cost savings as well as a reduction in the amount of hazardous material used.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A portable automated discrete fluid sample analyzer comprising:
 a pipettor movable between a plurality of receptacles and for extracting a fluid sample from at least one of the receptacles;
 a plurality of reaction cuvettes
 a pump;
 a microprocessor coupled to the pump and pipettor, for sending control signals to the pump and pipettor;
 a well configured to receive the fluid sample deposited by the pipettor;
 a sample preparation device in fluid communication with the well and the pump, wherein the fluid sample is transferred from the well to the sample preparation device by the pump under control of the microprocessor, the sample preparation device prepares the fluid sample by exposing it to an element within the sample preparation device in order to provide a prepared fluid sample, the prepared fluid sample is transferred back into the well by the pump under control of the microprocessor, the prepared fluid sample is removed from the well and is aspirated by the pipettor under control of the microprocessor for subsequent deposit of the prepared fluid sample into one of the reaction cuvettes; the pippettor, receptacles, reaction cuvettes, well, sample preparation device, and pump being mounted in a common housing which is portable.

2. The portable automated discrete fluid sample analyzer of claim 1, wherein the sample preparation device comprises a receptacle, the receptacle having the element, the element comprising one of a catalyst; a heating element; and a source of ultraviolet light.

3. The portable automated discrete fluid sample analyzer of claim 1, wherein the sample preparation device comprises means for agitating the fluid sample within the sample preparation device.

4. The portable automated discrete fluid sample analyzer of claim 3, wherein the means for agitating comprises the pump operated to create a cyclical motion of the fluid sample.

5. The portable automated discrete fluid sample analyzer of claim 1, further comprising a solenoid valve coupled to the microprocessor, the solenoid valve controlling flow of a rinse fluid into the sample preparation device.

6. The portable automated discrete fluid sample analyzer of claim 1, further comprising a detector.

7. The portable automated discrete fluid sample analyzer of claim 6, wherein the detector comprises at least one of a calorimeter, a photometer, and a conductance meter.

8. A method of sample preparation in a portable automated discrete fluid sample analyzer, the method comprising:
 mounting a pippettor, a plurality of receptacles, a plurality of reaction cuvettes, a microprocessor, a well, a sample preparation device, and a pump within a common housing which is portable;
 extracting a fluid sample with the pippettor from one of the receptacles in response to commands issued from the microprocessor;

providing the sample preparation device in fluid communication with the well;

depositing a fluid sample from the pipettor into the well in response to commands issued by the microprocessor;

pumping the fluid sample from the well into the sample preparation device in response to commands issued by the microprocessor;

exposing the fluid sample to an element within the sample preparation device in order to provide a prepared sample;

pumping the prepared sample from the sample preparation device back into the well in response to commands issued by the microprocessor;

removing the prepared sample from the sample preparation device with the pipettor in response to commands issued by the microprocessor;

aspirating the prepared sample into the pipettor; and depositing the prepared sample into one of the reaction cuvettes.

9. The method of claim 8, wherein exposing the fluid sample to an element within the sample preparation device further comprises exposing the fluid sample to one of a catalyst, a heating element, and a source of ultraviolet light.

10. The method of claim 9, wherein agitating the fluid sample comprises operating the pump to create a cyclical motion of the fluid sample.

11. The method of claim 8, further comprising agitating the fluid sample within the sample preparation device.

12. The method of claim 8, further comprising operating a solenoid valve for controlling flow of a rinse fluid into the sample preparation device.

13. The method of claim 12, wherein exposing the prepared sample in the reaction cuvette to the detector, comprises exposing the prepared sample to at least one of a calorimeter, a photometer, and a conductance meter.

14. The method of claim 8, further comprising exposing the prepared sample in a reaction cuvette to a detector.

* * * * *